United States Patent [19]

Descamps et al.

[11] Patent Number: 4,965,401
[45] Date of Patent: Oct. 23, 1990

[54] PROCESS FOR THE PREPARATION OF 2-PROPYL-2-PENTENOIC ACID AND ITS ESTERS

[75] Inventors: Marcel Descamps; Georges Sayac, both of Muret, France

[73] Assignee: Sanofi, Paris, France

[21] Appl. No.: 444,828

[22] Filed: Dec. 1, 1989

[30] Foreign Application Priority Data

Dec. 2, 1988 [FR] France .................. 88 15850

[51] Int. Cl.$^5$ ............................................ C07C 67/00
[52] U.S. Cl. ............................. 560/210; 562/532; 562/535
[58] Field of Search ............... 560/210; 562/532, 535

[56] References Cited

U.S. PATENT DOCUMENTS

| 3,177,226 | 4/1965 | Stilz et al. | 560/210 |
| 4,591,651 | 5/1986 | Delmas et al. | 560/210 |

FOREIGN PATENT DOCUMENTS

| 0293753 | 5/1988 | European Pat. Off. |
| 0069052 | 4/1985 | Japan. |

OTHER PUBLICATIONS

Beilsteins Handbuch der Organischen Chemie, 4iéme édition, vol. 2, 1920, Julius Springer Verlag, Berlin RAF, p. 452.

The Journal of Organic Chemistry, vol. 51, No. 9, 5/2/86, pp. 1735–1741, Amer. Chem. Society; J. A. Marshall et al.: "Condensation of Long-Chain Alpha-Phosphono Carboxylates with Aldehydes" p. 1736, Table 1; p. 1739, Table 3.

Chemische Berichte, vol. 99, No. 4, 1966, pp. 1198–1207, Verlag Chemie GmbH; H.-J. Bestmann et al.: "Eine Neue Synthese von Allen-Carbonsäureestern", p. 1203.

Bulletin of the Chemical Society of Japan, vol. 40, No. 12, Dec. 1967, pp. 2968–2970, K. Sasaki et al.: "Synthesis of Ethyl 5,9-Dimethyl-2,4,8-Decatrienoates and the Homologs".

Primary Examiner—Paul J. Killos
Attorney, Agent, or Firm—Wegner & Bretschneider

[57] ABSTRACT

The process for the preparation of the E isomers of the compounds of formula A:

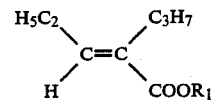

in which $R_1$ is selected from H or $C_1$–$C_4$ alkyl, comprises according to the invention the reaction of propionaldehyde with a phosphorus derivative of formula:

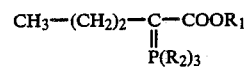

in which $R_1$ designates $C_1$–$C_4$ alkyl and $R_2$ is selected from $C_1$–$C_4$ alkyl or phenyl, and, optionally, the hydrolysis of the compound of formula A in which $R_1$ is alkyl in order to form the compounds of formula A in which $R_1$ is H.

Pharmaceutical industry.

5 Claims, No Drawings

PROCESS FOR THE PREPARATION OF 2-PROPYL-2-PENTENOIC ACID AND ITS ESTERS

The present invention relates to a process for the preparation of the E isomer of 2-propyl-2-pentenoic acid and its esters.

This acid, which has been described in particular in Arch. Pharm. 310(5) p. 394–403 (1977) and Journal of the American Chemical Society, 93, (17) p. 4242–4247 (1971), is a metabolite of valproic acid, a drug used in the treatment of epilepsy; this metabolite is expected to exhibit appreciable anti-epileptic activity and to be less teratogenic than valproic acid, and the development of a process for its preparation giving good yields of a pure product free of isomers was desirable in order to permit extensive clinical studies.

In fact, the processes described hitherto, whether it be dehydrohalogenation of the alpha bromo valproic acid of formula:

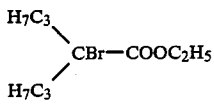

described in the article in Arch. Pharm previously cited, or the dehydration of the alpha hydroxy-acid described in the article in the Journal of the American Chemical Society previously cited, give a mixture of geometrical and even positional isomers of the 2-propyl-pentenoic acid, with an overall yield of the E isomer of the 2-propyl-2-pentenoic acid of only 25%.

It has now been found that this acid can be prepared in good yields from common starting materials without the formation of positional isomers and with very little of its geometrical isomer, starting from an ester of 2-bromo-valeric acid. Furthermore, the crude product obtained by saponification of the ester intermediate is sufficiently pure as to crystallize spontaneously.

The object of the invention is thus a process for the preparation of the E isomers of the compounds of formula A:

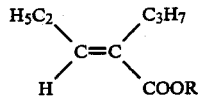

in which $R_1$ is selected from H or $C_1$–$C_4$ alkyl, wherein propionaldehyde is reacted with a phosphorus derivative of formula:

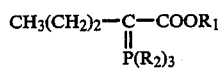

in which $R_1$ designates $C_1$–$C_4$ alkyl and $R_2$ is selected from $C_1$–$C_4$ alkyl or phenyl, in order to form an ester of 2-propyl-2-pentenoic acid of formula A, with the E configuration:

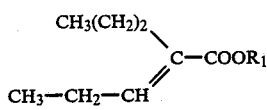

in which $R_1$ designates $C_1$–$C_4$ alkyl; the acid, $R_1$=H, a metabolite of valproic acid, can then be isolated after hydrolysis of the preceding ester.

The ylides of formula I can be prepared in the standard manner by the action of a base on a phosphonium salt of formula IV:

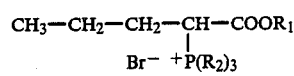

which results from the reaction of a trialkylphosphine or triphenylphosphine on an ester of 2-bromo-valeric acid of formula V:

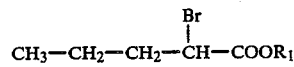

The ylide of formula I in which $R_2$ is $C_6H_5$ and $R_1$ is $C_2H_5$ has been described in Chem. Ber. 99 (4) 1198 (1966).

For example, triphenylphosphine is reacted at a temperature between 20° C. and 100° C. with the alpha bromo-ester dissolved in a polar aprotic solvent which does not contain functional groups with which phosphines can react, such as dimethylformamide and the salt obtained is treated with a strong base: an alkali metal hydroxide in aqueous medium or an alcoholate in alcoholic medium, in order to isolate the ylide of formula I.

The ylide (I) is then reacted with propionaldehyde under the standard conditions of the Wittig reaction. The condensation is carried out without a solvent or in an ether, for example, dioxan or tetrahydrofuran, preferably at a temperature higher than room temperature and very close to the reflux temperature of the solvent, optionally under slight pressure, lower than $5 \times 10^5$ Pa. The purification of the ester is carried out by distillation under reduced pressure in a conventional apparatus; the pressure is preferably from 1000 Pa to 5000 Pa.

In order to obtain the acid, the hydrolysis of the ester function is conducted in an acidic or basic aqueous alcoholic medium, the basic medium being preferred. The crude acid is crystallized from petroleum ether cooled to a temperature lower than −10° C.

The stereochemistry of the acid obtained was studied by nuclear magnetic resonance using the Nuclear Overhauser effect in the presence of a rare earth.

It was thus determined that the product has the E configuration according to the Ingold rules and may thus be represented by the structural formula:

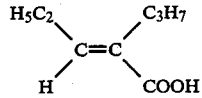

In the following, examples of the embodiment of the invention are described.

EXAMPLE 1

(a) 1-ethoxycarbonyl 1-butyl triphenylphosphonium bromide (formula IV, $R_1=C_2H_5$, $R_2=C_6H_5$).

3650 g of ethyl 2-bromovalerate and 4671 g of triphenylphosphine are introduced into 10 l of dimethylformamide and the mixture is maintained at 80° C. for 24 hours; after removal of the volatile products by distillation under reduced pressure, the residue is crystallized from diisopropyl ether to yield 6912 g of the phosphonium salt.

Yield: 84%.

(b) 1-ethoxycarbonyl 1-butene triphenylphosphorane (formula I, $R_1=C_2H_5$, $R_2=C_6H_5$).

6907 g of the salt obtained in the previous step are added to a stirred mixture of 21 l of water and 21 l of dichloromethane, followed by the gradual addition of 1030 ml of aqueous NaOH solution (33% wt/v). After 30 minutes' stirring, the organic phase is separated and the solvent is evaporated under reduced pressure after being washed with water and dried over $Na_2SO_4$. 11 l of hexane is added to the residue and the precipitate is isolated; after being dried, it weighs 5283 g.

Yield: 92.3%.

(c) Ethyl 2-propyl-2-pentenoate (formula A, $R_1=C_2H_5$).

5220 g of the ylide obtained according to (b) are dissolved in 8.5 l of dioxan, then 2.9 l of propionaldehyde are added. After 24 hours at reflux temperature the excess aldehyde and the solvent are distilled under reduced pressure and 10 l of ethyl ether are added to the residue. The precipitate of triphenylphosphine oxide formed is separated and the solvent is removed under reduced pressure; the ester is then distilled at 90°–92° C. under 2700 Pa. 1492 g of the ester with the E configuration are obtained, contaminated with 4% of ester with the Z configuration.

Yield based on the alpha bromo ester: 51%.

NMR spectrum: (250 MHz—TMDS standard; solvent $CDCl_3$) 6.7 ppm (triplet, 1H); 4.2 ppm (quadruplet, 2H); 2.4 ppm (quadruplet, 4H); 1 ppm (multiplet, 11H).

EXAMPLE 2

Ethyl 2-propyl-2-pentenoate.

A mixture of 728 g of ylide obtained by application of the process described in Example 1b and 830 ml of propionaldehyde is maintained at 80° C. for 24 hours under a pressure of $3 \times 10^5$ Pa. The excess aldehyde is then removed by distillation under reduced pressure; the precipitate formed after addition of 6 l of diisopropyl ether to the residue is removed and the solvent, followed by the desired ester, are distilled under reduced pressure. 196 g of ester are isolated.

Yield: 48% based on the alpha bromo ester.

EXAMPLE 3

2-propyl-2-pentenoic acid (E isomer); 1466 g of ester prepared according to Example 1 or 2 are introduced into a solution of 4620 g of KOH in 10.6 l of aqueous ethanol (50/50-v/v).

After 75 minutes at reflux temperature the mixture is allowed to return to room temperature. It is then poured slowly with stirring onto 20 kg of crushed ice and 9 l of a 10N aqueous solution of hydrochloric acid. When the whole mixture has attained room temperature the acid is extracted twice from the aqueous phase with 9 l of hexane; the organic phases are combined, washed, dried and the solvent is distilled under reduced pressure.

1 l of petroleum ether is added to the residue and the precipitate which formed after several hours at −20° C. is isolated. It consists of 1024 g of the desired acid with the E configuration and melts at 33° C. Yield: 83.6%

NMR spectrum: (250 MHz-solvent: $CDCl_3$, internal standard TMDS) 12.3 ppm (singlet, 1H); 6.8–7.1 ppm (triplet, 1H); 2–2.5 ppm (multiplet, 4H); 1.2–1.7 ppm (multiplet, 2H); 0.7–1.2 ppm (multiplet, 6H).

Various salts of the E isomer of 2-propyl-2-pentenoic acid have been prepared.

Potassium salt 20 g of 2-propyl-2-pentenoic acid are dissolved in 200 ml of ethanol; an ethanolic solution of 8.0 g of potassium hydroxide pellets in 88 ml of ethanol is added.

After being stirred for 1 hour at room temperature, the solvent is removed and the residue is taken up in acetone and evaporated to dryness. The potassium salt of 2-propyl-2-pentenoic acid, E isomer, solidifies from hexane: 9.44 g of product are obtained.

Magnesium salt 7.1 g of 2-propyl-2-pentenoic acid, E isomer, and 1.456 g of magnesium hydroxide are dissolved in 250 ml of water at 50° C.: the solution obtained is lyophilized and the residue is crystallized from acetone. 4.5 g of the magnesium salt of 2-propyl-2-pentenoic acid, E isomer, are obtained.

Calcium salt 5 g of sodium 2-propyl-2-pentenoate, E isomer, are stirred in 20 ml of boiled water and a solution of 2.29 g of calcium chloride dihydrate in 10 ml of boiled water is added in the presence of an antioxidant (hydroquinone). The precipitate obtained is filtered off and washed with water and acetone. 2.85 g of calcium 2-propyl-2-pentenoate, E isomer, are obtained.

We claim:

1. A process for the preparation of the E isomers of the compounds of formula A:

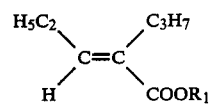

in which $R_1$ is selected from H or $C_1$–$C_4$ alkyl, wherein propionaldehyde is reacted with a phosphorus derivative of formula:

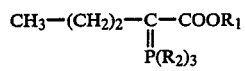

in which $R_1$ designates $C_1$–$C_4$ alkyl and $R_2$ is selected from $C_1$–$C_4$ alkyl or phenyl, and optionally the compound of formula A in which $R_1$ is alkyl is hydrolyzed to form the compound of formula A in which $R_1$ is H.

2. Process according to claim 1, wherein the reaction is carried out in a polar aprotic solvent at a temperature between 20° C. and 100° C.

3. Process according to claim 2, wherein the reaction is carried out in dioxan at reflux.

4. Process according to claim 1, wherein the hydrolysis of the ester of formula A is conducted in basic aqueous alcoholic medium.

5. Process according to claim 1, wherein the ester is distilled under reduced pressure before the hydrolysis and the acid is crystallized from petroleum ether at a temperature below −10° C.